United States Patent
Lee et al.

(10) Patent No.: US 9,134,420 B2
(45) Date of Patent: Sep. 15, 2015

(54) THREE-DIMENSIONAL (3D) ULTRASOUND SYSTEM FOR SCANNING OBJECT INSIDE HUMAN BODY AND METHOD FOR OPERATING 3D ULTRASOUND SYSTEM

(75) Inventors: Kwang-Hee Lee, Daejeon (KR); Sung-Yun Kim, Gyeonggi-Do (KR)

(73) Assignee: SAMSUNG MEDISON CO., LTD., Hongcheon-gu, Gangwon-do (KR)

( * ) Notice: Subject to any disclaimer, the term of this patent is extended or adjusted under 35 U.S.C. 154(b) by 960 days.

(21) Appl. No.: 12/943,623

(22) Filed: Nov. 10, 2010

(65) Prior Publication Data
US 2011/0224546 A1 Sep. 15, 2011

(30) Foreign Application Priority Data

Mar. 10, 2010 (KR) .......... 10-2010-0021136
May 26, 2010 (KR) .......... 10-2010-0049028

(51) Int. Cl.
*A61B 8/00* (2006.01)
*G01S 15/89* (2006.01)
*A61B 8/08* (2006.01)
(Continued)

(52) U.S. Cl.
CPC ........... *G01S 15/8993* (2013.01); *A61B 8/0866* (2013.01); *A61B 8/145* (2013.01); *G06T 7/60* (2013.01); *G06T 19/00* (2013.01); *G01S 7/52063* (2013.01); *G06T 2207/10136* (2013.01); *G06T 2207/30044* (2013.01); *G06T 2210/41* (2013.01);
(Continued)

(58) Field of Classification Search
CPC .......... A61B 5/06; A61B 5/1127; A61B 6/12; A61B 6/5235; A61B 6/5241; A61B 6/5247; A61B 6/506

USPC .......... 600/407, 437, 443, 448–457; 324/6.12
See application file for complete search history.

(56) References Cited

U.S. PATENT DOCUMENTS 6,585,647 B1 * 7/2003 Winder .......... 600/437
2005/0096540 A1 5/2005 Ooshima
(Continued)

FOREIGN PATENT DOCUMENTS

JP 62-193822 8/1987
JP 2005-087634 A 4/2005
(Continued)

OTHER PUBLICATIONS

Korean Notice of Allowance, w/ English translation thereof, issued in Korean Patent Application No. 10-2010-0049028, dated Feb. 3, 2012.
(Continued)

*Primary Examiner* — Unsu Jung
*Assistant Examiner* — Joel Lamprecht
(74) *Attorney, Agent, or Firm* — McDermott Will & Emery LLP

(57) ABSTRACT

Provided is a three-dimensional (3D) ultrasound system and a 3D ultrasound system operating method that may obtain 3D ultrasound data with respect to an object inside a human body to determine an accurate sagittal view. The 3D ultrasound system may include a scanner to generate ultrasound data including image data generated by scanning an object inside a human body, a processing unit to detect a center point of the object from the generated ultrasound data, and to generate, on the ultrasound data, a virtual plane on which the detected center point is placed, and a controller to rotate the ultrasound data based on the image data included in the virtual plane and to determine a sagittal view with respect to the object.

15 Claims, 4 Drawing Sheets

(51) Int. Cl.
  *A61B 8/14* (2006.01)
  *G06T 7/60* (2006.01)
  *G06T 19/00* (2011.01)
  *G01S 7/52* (2006.01)

(52) U.S. Cl.
  CPC ... *G06T 2219/008* (2013.01); *G06T 2219/2016* (2013.01)

(56) References Cited

U.S. PATENT DOCUMENTS

2005/0251036 A1* 11/2005 Abuhamad ............... 600/437
2007/0081705 A1* 4/2007 Carneiro et al. ............ 382/128
2008/0123922 A1* 5/2008 Gielen et al. .............. 382/131
2008/0188748 A1 8/2008 Sonek et al.

FOREIGN PATENT DOCUMENTS

KR 10-2008-0004775 A 1/2008
WO 2009-136332 A2 11/2009

OTHER PUBLICATIONS

Extended European Search Report issued in corresponding EP Application No. 11150363.7, dated Sep. 12, 2013.
Chung, B.L., et al.: "The application of three-dimensional ultrasound to nuchal translucency measurement in early pregnancy (10-14 weeks): a preliminary study", Ultrasound in Obstetrics and Gynecology, Feb. 1, 2000, vol. 15, pp. 122-125.
H. Abele et al., "Effect of Deviation from the Mid-sagittal Plane on the Measurement of Fetal Nuchal Translucency," Ultrasound Obstet Gynecol, Feb. 24, 2010, vol. 35, pp. 525-529.
G. Clementschitsch et al., "Comparison between two- and three-dimensional ultrasound measurements of nuchal translucency," Ultrasound Obstet Gynecol, 2001, vol. 18, pp. 475-480.
F. Molina et al., "Frontomaxillary facial angle in trisomy 21 fetuses at 16-24 weeks of gestation," Ultrasound Obstet Gynecol, 2008, vol. 31, pp. 384-387.
Lee et al., "Robust border enhancement and detection for measurement of fetal nuchal translucency in ultrasound images," Med Bio Eng Comput (2007) 45:1143-1152.
Japanese Office Action issued in Japanese Application No. 2011-003019 dated Oct. 7, 2014, w/English translation.

* cited by examiner

210

220

THREE-DIMENSIONAL (3D) ULTRASOUND SYSTEM FOR SCANNING OBJECT INSIDE HUMAN BODY AND METHOD FOR OPERATING 3D ULTRASOUND SYSTEM

CROSS-REFERENCE TO RELATED APPLICATION(S)

This application claims the benefit of Korean Patent Application Nos. 10-2010-0021136 and 10-2010-0049028, respectively filed on Mar. 10, 2010 and May 26, 2010, in the Korean Intellectual Property Office, the disclosures of which are incorporated herein by references.

BACKGROUND

1. Field

The present invention relates to a three-dimensional (3D) ultrasound system of scanning an object inside a human body and a method of operating the 3D ultrasound system.

2. Description of the Related Art

An ultrasound system may transmit, from the surface of a human body, an ultrasound signal toward a predetermined portion inside the human body, for example, a fetus, an organ, and the like, to obtain an image associated with a section of soft tissue or the bloodstream by using information of the ultrasound signal having been reflected from tissue inside the body.

The ultrasound system has an advantage of being small, inexpensive, displayable in real time, and reliable since a subject is not exposed to an X-ray and the like and thus, the ultrasound system is widely used together with other image diagnostic devices, such as a computerized tomography (CT) scanner, a magnetic resonance image (MRI) device, a nuclear medicine device, and the like.

A fetus having Down's syndrome is generally identified based on a scheme of measuring a thickness of a nuchal translucency (NT) of the fetus. The scheme was designed by Nicolaides, in 1992. When the fetus has Down's syndrome, a thick NT is observed since body fluid is accumulated in a subcutaneous tissue of a neck.

Specifically, when the fetus has a chromosomal anomaly or a deformity of the heart, a thick NT is often observed. Therefore, a physician may measure a thickness of the NT of the fetus through the ultrasound system, and may observe the fetus using a Chorionic Villus sampling scheme or an amniocentesis scheme when the thickness is over 2.5 mm.

As another scheme of identifying Down's syndrome in a fetus, an angle between the palate and the dorsum nasi, namely, the frontmaxillary facial (FMF) angle, may be measured. The FMF angle of a normal fetus is 78.1 degrees, and a fetus having an FMF angle of 88.7 degrees has a high possibility of having Down's syndrome. There are various schemes for identifying Down's syndrome, such as measuring the biparietal diameter (BPD), Head Circumference (HC), Abdominal Circumference (AC), Femur Length (FL), and the like. A gestational age and a weight of the fetus may be estimated based on the schemes.

A process of obtaining an accurate sagittal view from ultrasound data needs to be performed in advance, to identify Down's syndrome in the fetus by measuring the thickness of the NT and the FMF angle between the palate and the dorsum nasi.

Conventionally, however, the sagittal view is determined based on experience of the physician and thus, the measured thickness of the NT of the fetus or the FMF angle between the palate and the dorsum nasi may be different from an actual thickness and an actual angle. Accordingly, there has been a difficulty in making an accurate diagnosis.

SUMMARY

An aspect of the present invention provides a three-dimensional (3D) ultrasound system and a 3D ultrasound system operating method that may detect a center point of an object inside a human body from 3D ultrasound data with respect to the object, may rotate the ultrasound data using image data included in a virtual plane on which the detected center point is placed and thus, may automatically determine an accurate sagittal view with respect to the object.

Another aspect of the present invention provides a 3D ultrasound system and a 3D ultrasound system operating method that may measure, from ultrasound data determined as a sagittal view, a thickness of an NT of a fetus or an FMF angle between a dorsum nasi of the fetus and a palate of the fetus, to accurately diagnose whether the fetus has an abnormality, when an object is the fetus.

Another aspect of the present invention provides a 3D ultrasound system and a 3D ultrasound system operating method that may finely rotate ultrasound data to redetermine a sagittal view.

Another aspect of the present invention provides a 3D ultrasound system and a 3D ultrasound system operating method that may determine a direction of a head of a fetus, may select, as a reference axis, a location of a falx included in data where data obtained by scanning the falx in the determined direction of the head is outputted to be brightest and thus, the reference axis used for rotating the ultrasound data to determine the sagittal view may be determined.

According to example embodiments, there may be provided a 3D ultrasound system, the system including a scanner to generate ultrasound data including image data generated by scanning an object inside a human body, a processing unit to detect a center point of the object from the generated ultrasound data, and to generate, on the ultrasound data, a virtual plane on which the detected center point is placed, and a controller to rotate the ultrasound data based on the image data included in the virtual plane and to determine a sagittal view with respect to the object.

According to example embodiments, there may be provided a 3D ultrasound system operating method, the method including generating ultrasound data including image data generated by scanning an object inside a human body, detecting a center of the object from the generated ultrasound data, generating, on the ultrasound data, a virtual plane on which the detected center point is placed, and determining a sagittal view with respect to the object by rotating the ultrasound data based on the image data included in the virtual plane.

Additional aspects and/or advantages will be set forth in part in the description which follows and, in part, will be apparent from the description, or may be learned by practice of the embodiments.

Effect

According to embodiments, an accurate sagittal view may be automatically determined by three-dimensional (3D) ultrasound data with respect to an object inside a human body.

According to embodiments, whether a fetus has an abnormality may be accurately diagnosed by measuring, from ultrasound data determined as a sagittal view, a thickness of an NT of the fetus or an FMF angle between a dorsum nasi of the fetus and a palate of the fetus, when an object is the fetus.

According to embodiments, a sagittal view may be redetermined based on a fine movement of a fetus.

According to embodiments, a sagittal view may be reliably determined by determining a direction of a head of a fetus, and selecting, as a reference axis, a location of a falx included in data where data obtained by scanning the falx in the determined direction of the head is outputted to be brightest

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
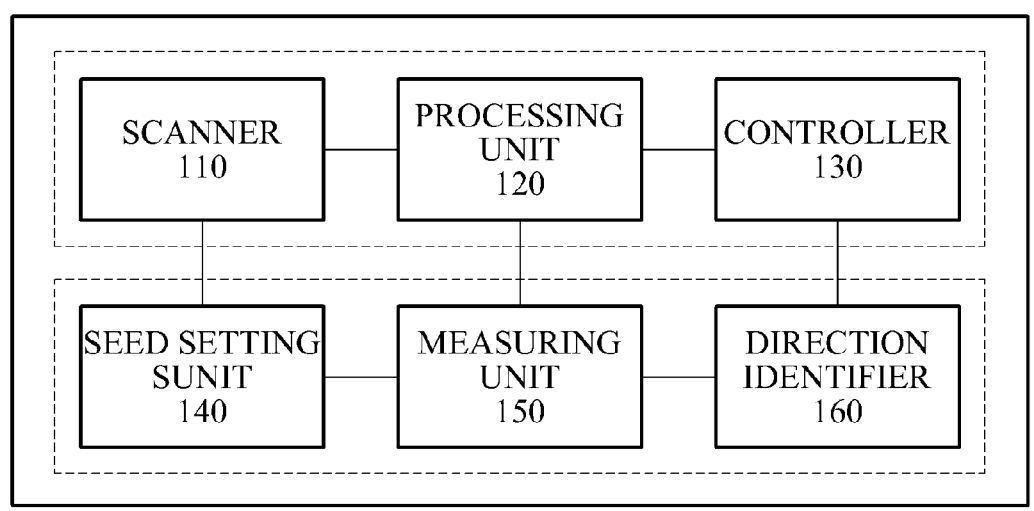
FIG. 1 is a diagram illustrating an internal configuration of a 3D ultrasound system according to an embodiment of the present invention.

Reference will now be made in detail to example embodiments, examples of which are illustrated in the accompanying drawings, wherein like reference numerals refer to the like elements throughout.

FIG. 1 illustrates an internal configuration of a three-dimensional (3D) ultrasound system 100 according to an embodiment of the present invention.

Referring to FIG. 1, the 3D ultrasound system 100 may include a scanner 110, a processing unit 120, and a controller 130.

The scanner 110 may generate ultrasound data including image data generated by scanning an object inside a human body. The object inside the human body may be a fetus, an organ, and the like. The scanner 110 may generate, as the ultrasound data, the image data generated by scanning the fetus, the organ, and the like.

As an example of generating the ultrasound data, the scanner 110 may set a region of interest (ROI) with respect to the object and may locate a seed in the set ROI. In this example, when the object is the fetus, the seed may be located adjacent to an NT of the fetus. The scanner 110 may generate the image data by scanning the object using a 3D ultrasound to generate the ultrasound data with respect to the object. An area occupied by the object in the generated ultrasound data may be the generated image data.

The processing unit 120 may detect a center point of the object from the generated ultrasound data, and may generate a virtual plane on which the detected center point is placed. The processing unit 120 may generate the virtual plane including the detected center point on the ultrasound data and thus, may form a B-Plane. For example, the B-Plane may be a plane displaying image data viewed from a head of the fetus.

For example, when the object inside the human body is the fetus, the processing unit 120 may determine, from the generated ultrasound data, a first feature point associated with a dorsum nasi of the fetus, may determine a second feature point associated with a palate of the fetus based on the determined first feature point, and may detect the center point of the object, namely, a head of the fetus, based on the second feature point.

Specifically, the processing unit 120 may determine the first feature point associated with the dorsum nasi of the fetus based on the seed located adjacent to the NT of the fetus from an A-Plane, the A-Plane illustrating a side of the fetus, and may determine the second feature point associated with the palate based on the first feature point. The processing unit 120 may detect the center point of the head of the fetus from the A-Plane based on the first feature point and the second feature point. A point in the ultrasound data may be determined as the center point of the head of the fetus, and the point may be experimentally determined, to be close to an actual center of the head, based on years of experiences and experimentations. For example, a point located several centimeters apart from the second feature point, from among points included in a virtual line generated between the first feature point and the second feature point.

The processing unit 120 may generate, on the ultrasound data, the B-plane, namely, a virtual plane that includes the detected center point of the head of the fetus and is vertical to the A-Plane.

For reference, the processing unit 120 may approximately determine the first feature point, the second feature point, and the center point by appropriately combining and utilizing a well-known algorithm and an image processing with respect to the ultrasound data, and by utilizing integrated data based on years of experiences and experimentations.

The controller 130 may rotate the ultrasound data based on the image data included in the virtual plane to determine a sagittal view with respect to the object. When the B-Plane is rotated, the A-Plane being vertical to the B-Plane may be interoperably rotated. The controller 130 may enable the A-plane to be the sagittal view based on the rotation of the B-plane. When the object is the fetus, the image data included in the virtual plane may be an area corresponding to the object viewed from a direction of the head of the fetus.

For example, the controller 130 may match a figure corresponding to the image data with the image data included in the virtual plane, and may rotate the ultrasound data to enable an axis constituting the matched figure to be parallel with a predetermined reference axis.

The reference axis may be a line used as a reference when the ultrasound data is rotated to correct the ultrasound data to generate the sagittal view. The 3D ultrasound system 100 may further include a direction identifier 160 to select the reference axis.

When the object is the fetus, the direction identifier 160 may identify a direction of the head of the fetus from the ultrasound data. Features of the scanned fetus may be identified from the ultrasound data including a vague shape of the fetus, by identifying the direction of the head of the fetus.

The direction identifier 160 may estimate the direction of the head by scoring with respect to an FMF angle. The direction identifier 160 may obtain a plurality of slice data with respect to a side direction of the ultrasound data, and may determine the direction of the head of the fetus based on an FMF angle of each slice data measured by the measuring unit 150.

A process where the direction identifier 160 identifies the direction of the head may be described.

The direction identifier 160 may detect a nasal bridge from each slice data of the A-Plane and may perform scoring with respect to the detected nasal bridge.

1) Top-Hat Transform

The direction identifier 160 may apply a top-hat transform to the ultrasound data to detect the nasal bridge and the palate.

The top-hat transform is applied to the ultrasound data to compensate for weak points of other schemes utilized for restoring an original image, for example, an edge detection scheme or a scheme of applying a threshold to the original image. When the original image of the fetus is restored based on the edge detection scheme, the edge detection scheme may have a weak point in restoring a boundary of the fetus, a boundary of the ultrasound data, and other tissues of the mother, together with an original image of the fetus. The scheme of applying threshold to the original image may have a weak point of restoring an image of skin of the fetus, the placenta of the mother, and the like which are relatively bright compared with a background, together with the original image of the fetus.

The direction identifier 160 may restore the image of the fetus in the ultrasound data by applying top-hat transform to the ultrasound data, to remove the obstructive factors. The top-hat transform may be a well-known scheme and thus, a detailed example of using the top-hat transform is omitted.

2) Adaptive Thresholding

The direction identifier 160 may apply a threshold with respect to an image generated by applying the top-hat transform to the ultrasound data, the threshold being generated by appropriately combining a mean and a standard deviation of an entire image. The direction identifier 160 may obtain, from the ultrasound data, a thresholded image from which bright details including the nasal bridge and the palate are extracted.

The direction identifier 160 distinguishes the nasal bridge and the palate from the ultrasound data by applying top-hat transform and an adaptive threshold to the ultrasound data.

3) Detection of Nasal Bridge Line (NBL)

The direction identifier 160 may detect a nasal bridge line (NBL) from the thresholded image, and may estimate the direction of the head of the fetus based on an angle of a slope of the NBL.

For example, when the NBL of the thresholded image may have a slope of '\', the direction identifier 160 may estimate the direction of the head of the fetus based on the slope and an FMF angle between the NBL and the palate, as being on the left on the A-Plane.

4) Scoring

Arms of the fetus, the placenta of the mother, and bright regions of other tissues exist around the head of the fetus. Therefore, when the direction of the head of the fetus is estimated by only detecting an NBL for a A-Plane of an initial plane, a great number of errors may occur. A nasal bridge or a zygomatic bone is symmetrical around a face of the fetus and thus, the direction identifier 160 may obtain plurality of slice data with respect to the side direction of the ultrasound data based on the initial plane, may determine an NBL for each of the plurality of obtained slice data, and may perform scoring with respect to a direction estimated from each slice data, to detect an accurate direction of the head.

For example, when ten slice data are obtained from the ultrasound data, the direction identifier 160 may perform scoring with respect to the direction of the head estimated from each slice data, as 'left:right=7:3'. Therefore, the left having a relatively higher score may be determined as the direction of the head of the fetus.

The controller 130 may select, as a reference axis, a location of a falx included in a reference image having a highest brightness intensity among reference images obtained by scanning the falx of the fetus in the determined direction of the head. The controller 130 may determine, as the reference axis used for obtaining the sagittal view, the location where the reference image outputted to be brightest.

When the A-plane is used for a mid-sagittal view, a falx cerebri region is evenly bright, the A-plane showing a side of the fetus. However, when the A-Plane is not used for mid-sagittal view, the falx cerebri region may not evenly bright, and may have a dark region.

The controller 130 may move and rotate the ultrasound data based on a center of the head and may determine a case where the falx region is brightest and is evenly distributed, as the mid-sagittal view, namely, the reference axis for determining the sagittal view.

The rotation of the ultrasound data performed by the controller 130 will be described again. As another example, the controller 130 may match a figure with image data included in the virtual plane, and may rotate the ultrasound data by an angle between an axis constituting the matched figure and the predetermined reference axis.

For example, the controller 130 may determine the figure matched with the image data as an oval. In this example, the controller 130 may focus on, using a predetermined color or a predetermined line, the figure matched with the image data to display the focused figure on a display screen. When the figure matched with the image data is determined as the oval, the controller 130 may display, on the display screen, information associated with at least one of a major axis, a minor axis, and a circumference of the oval.

The controller 130 may rotate the ultrasound data to enable the major axis of the oval to be parallel with a reference axis of the image data, the major axis passing a center point of the object and the reference axis being a vertical axis or a y axis. The controller 130 may rotate the ultrasound data by an angle between the major axis of the oval and the reference axis of the image data.

According to an embodiment, an accurate sagittal view may be automatically determined based on 3D ultrasound data with respect to the object inside the human body.

The controller 130 may finely rotate the ultrasound data based on a manipulation of an operator to redetermine the sagittal view. Accordingly, when the object is the fetus, the controller 130 may finely rotate the ultrasound data based on the manipulation of the operator, and the manipulation may be based on a fine movement of the fetus and thus, a more accurate sagittal view may be determined.

According to another embodiment, the 3D ultrasound system 100 may further include a seed setting unit 140 and a measuring unit 150.

When the object inside a human body is the fetus, the seed setting unit 140 may set a seed around the NT of the fetus in the ultrasound data, the ultrasound data being determined as the sagittal view by performing the rotation.

The measuring unit 150 may automatically measure, from the ultrasound data determined as the sagittal view, a thickness of the NT of the fetus based on the set seed to display the measured thickness on the display screen.

Therefore, the operator or a physician may more accurately diagnose whether the fetus has an abnormality, based on the measured thickness of the NT of the fetus. In this example, the measuring unit 150 may focus on the NT of the fetus in the ultrasound data, using a predetermined color or a predetermined line, and may display the focused around the seed.

According to another embodiment, the measuring unit 150 may automatically measure, from the ultrasound data determined as the sagittal view, an FMF angle between the first feature point associated with the dorsum nasi of the fetus and the second point associated with the palate of the fetus, and may display the measured FMF angle on the display screen.

Therefore, the operator or the physician may more accurately diagnose whether the fetus has an abnormality, based on the measured FMF angle. In this example, the measuring unit 150 may focus the first feature point and the second feature point in the ultrasound data, using a predetermined color or a predetermined line to display on the display screen.

In this example, when the sagittal view is redetermined by finely rotating the ultrasound data based on the manipulation of the operator, the measuring unit 150 may edit the measured thickness of the NT of the fetus, the measured FMF angle, the circumference of the figure matched with the image data, for example the circumference of the oval, and the like.

Therefore, according to an embodiment, when the object is the fetus, the thickness of the NT of the fetus or the FMF angle between the dorsum nasi and the palate of the fetus are measured from the ultrasound data determined as the sagittal view and thus, whether the fetus has an abnormality may be accurately diagnosed.

Figure 2:
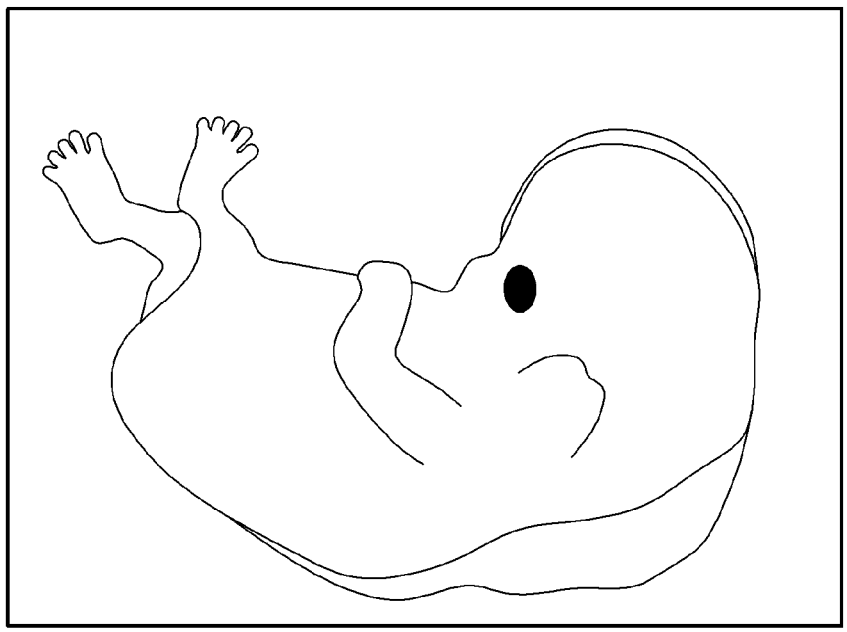
FIG. 2 is a diagram illustrating an object inside a human body and ultrasound data generated by scanning the object according to an embodiment of the present invention.
Figure 2:
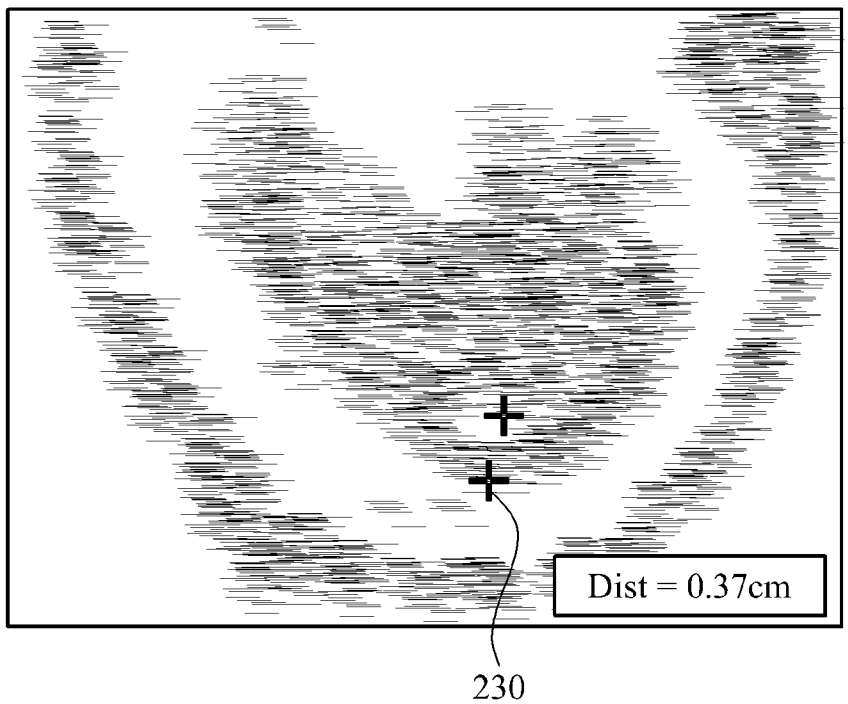

FIG. 2 illustrates a fetus 210 inside a human body and ultrasound data 220 generated by scanning the fetus 210 according to an embodiment of the present invention.

Referring to FIG. 2, a 3D ultrasound system may scan the fetus 210 using a 3D ultrasound system, to generate the ultrasound data 220. In this example, an area corresponding to the fetus 210 in the generated ultrasound data 220 may be image data. A seed may be located around an NT 230 of the fetus 210.

The 3D ultrasound system may automatically measure, from the ultrasound data 220 determined as a sagittal view, a thickness of the NT 230 of the fetus 210 based on a set seed, and may display the measured NT on a display screen. Therefore, an operator or a physician may more accurately diagnose whether the fetus 210 has an abnormality, based on the measured thickness of the NT 230 of the fetus 210. In this example, the measuring unit 150 may focus on the NT 230 of the fetus 210 in the ultrasound data 220, using a predetermined color or a predetermined line, and may display the focused NT 230 around the seed.

Figure 3:
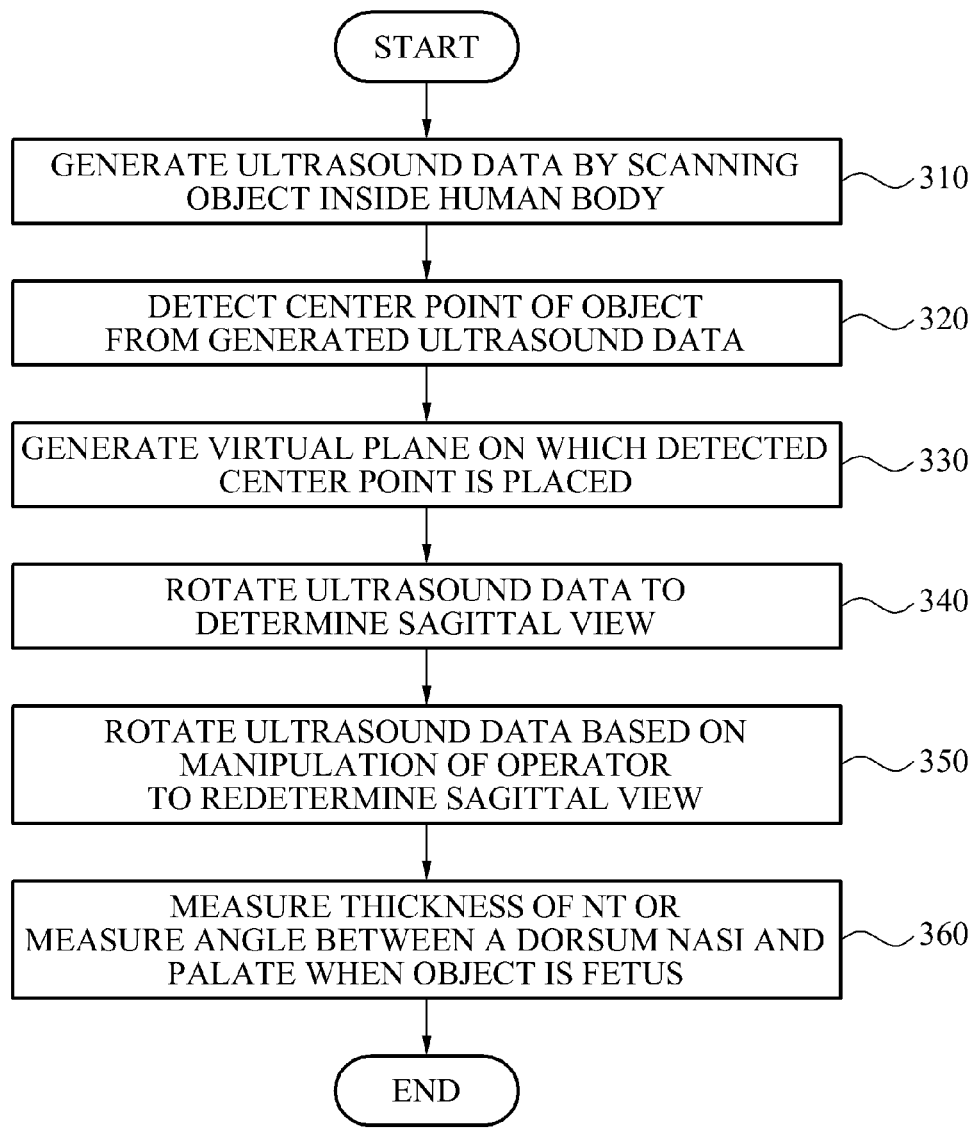
FIG. 3 is a flowchart illustrating a 3D ultrasound system operating method according to an embodiment of the present invention.

FIG. 3 illustrates a 3D ultrasound system operating method according to an embodiment of the present invention.

According to an embodiment, the 3D ultrasound system operating method may be embodied by the 3D ultrasound system 100. The 3D ultrasound system operating method may be described with reference to FIGS. 1 and 3.

In operation 310, the 3D ultrasound system 100 generates ultrasound data including image data generated by scanning an object inside a human body.

In this example, the object inside the human body may be a fetus and an organ.

For example, the scanner 110 may set an ROI with respect to the object, and may locate a seed in the set ROI. When the object is the fetus, the seed may be located around an NT of the fetus. The scanner 110 may scan the object using a 3D ultrasound to generate ultrasound data. An area corresponding to the object in the generated ultrasound data may be image data.

In operations 320 and 330, the 3D ultrasound system 100 detects a center point of the object from the generated ultrasound data, and the 3D ultrasound system 100 generates, on the ultrasound data, a virtual plane on which the detected center point is placed.

For example, when the object inside the human body is the fetus, the processing unit 120 determines, from the generated ultrasound data, a first feature point associated with a dorsum nasi of the fetus, determines a second feature point associated with a palate of the fetus based on the determined first feature point, and detects the center point of the object based on the determined second feature point, namely, a center point of a head of the fetus.

Specifically, the processing unit 120 determines the first feature point associated with the dorsum nasi based on the seed located around the NT of the fetus from the A-Plane, the A-Plane illustrating a side of the fetus, and may determine the second feature point associated with the palate based on the first feature point. The processing unit 120 may determine the center point of the head of the fetus from the A-Plane, based on the first feature point and the second feature point. The processing unit 120 may generate the B-Plane that is a virtual plane including the determined center point of the head of the fetus and being vertical to the A-Plane.

For reference, the processing unit 120 may determine the first feature point, the second feature point, and the center point, using a predetermined algorithm and image processing with respect to the ultrasound data or using integrated data based on years of experimentations.

In operation 340, the 3D ultrasound system 100 rotates the ultrasound data using the image data included in the virtual plane, and determines the sagittal view with respect to the object.

The image data may be an area corresponding to the object, for example, the fetus, in the virtual plane.

For example, the controller 130 may determine a figure matched with the image data as an oval. In this example, the controller 130 may focus on the figure matched with the image data using a predetermined color or a predetermined line to display the focused figure on a display screen. When the figure matched with the image data is determined as the oval, the controller 130 may display, on the display screen, information associated with at least one of a major axis, a minor axis, a circumference of the oval.

The controller 130 may rotate the ultrasound data to enable the major axis of the oval to be parallel with a reference axis of the image data, the major axis of the oval passing the center point of the object and the reference axis of the image data being a vertical axis or a y axis.

A process of setting the reference axis may be described with reference to FIG. 4.

Figure 4:
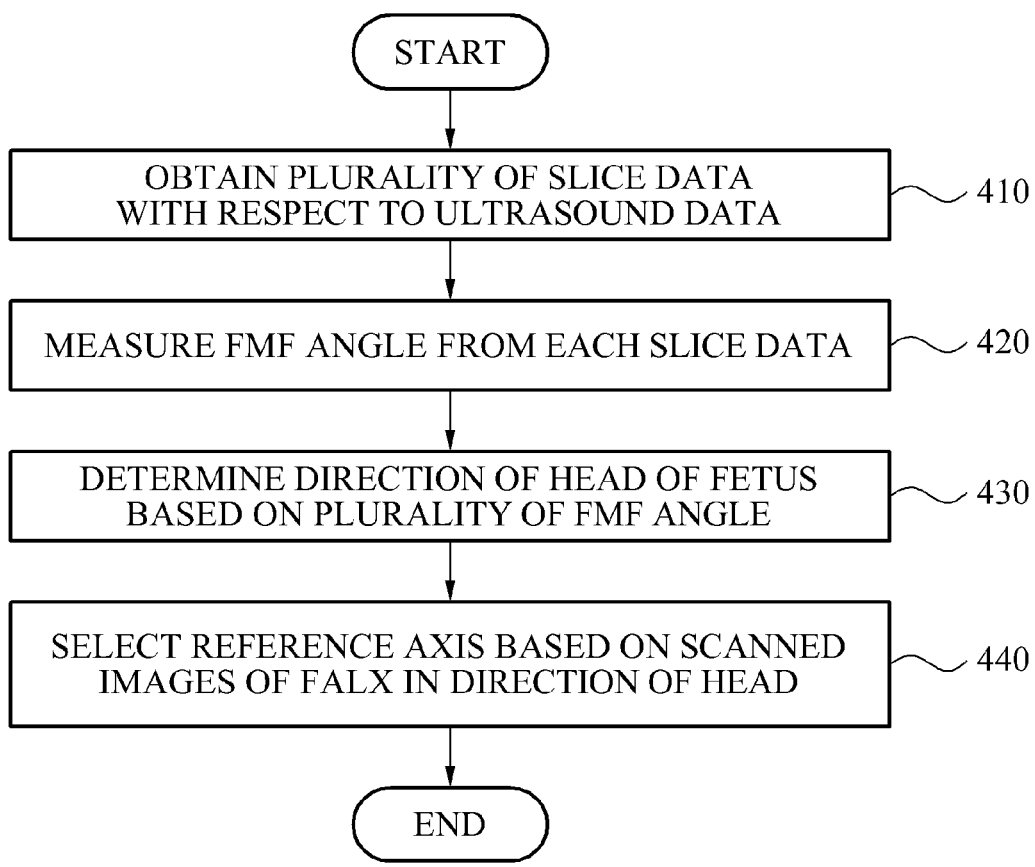
FIG. 4 is a flowchart illustrating a process of setting a reference axis according to an embodiment of the present invention.

FIG. 4 illustrates a process of setting a reference axis according to an embodiment of the present invention.

When an object is a fetus, the 3D ultrasound system 100 obtains a plurality of slice data with respect to a side direction of ultrasound data in operation 410. The 3D ultrasound system 100 may obtain the plurality of slice data with respect to the side direction of the ultrasound data based on an initial plane of A-Plane.

In operation 420, the 3D ultrasound system 100 measures an FMF angle between a first feature associated with a dorsum nasi of the fetus and a second feature point associated with a palate of the fetus, with respect to each slice data. The 3D ultrasound system 100 measures the FMF angle between a nasal bridge and a palate, and particularly, measures a direction where the FMF angle is formed.

In operation 430, the 3D ultrasound system 100 determines a direction of a head of the fetus based on an FMF angle measured with respect to each slice data. The 3D ultrasound system 100 performs scoring with respect to the direction of the head determined in each slice data, and determines a direction having a relatively higher score as the direction of the head of the fetus.

For example, when ten slice data are obtained from the ultrasound data, the 3D ultrasound system 100 may perform scoring with respect to the direction of the head estimated from each slice data, as 'left:right=7:3'. Therefore, the left having a relatively higher score may be determined as the direction of the head of the fetus.

In operation 440, the 3D ultrasound system 100 determines, as the reference axis, a location of a falx included in a reference image having a highest brightness intensity among reference images obtained by scanning the falx of the fetus in the determined direction of the head. The 3D ultrasound system 100 may determine, as the reference axis used for obtaining a sagittal view, the location where the reference image is outputted to be brightest.

Referring again to FIG. 3, the controller 130 of the 3D ultrasound system 100 may rotate the ultrasound data by an angle between a major axis of an oval and a reference axis of image data, the major axis passing a center point of the object and the reference axis being a vertical axis or a y axis.

According to an embodiment, the 3D ultrasound data with respect to an object inside a human body may automatically determine an accurate sagittal view.

In operation 350, the 3D ultrasound system 100 finely rotates the ultrasound data based on a manipulation of an operator to redetermine the sagittal view.

Therefore, when the object is the fetus, the controller 130 may finely rotate the ultrasound data based on the manipulation of the operator, and the manipulation may be based on a fine movement of the fetus and thus, a more accurate sagittal view may be determined.

In operation 360, when the object inside the human body is the fetus, the 3D ultrasound system 100 automatically measures, from the ultrasound data determined as the sagittal view, a thickness of an NT of the fetus, based on a set seed, or automatically measures, from the ultrasound data determined as the sagittal view, an FMF angle between a first feature point associated with a dorsum nasi of the fetus and a second feature point associated with a palate of the fetus.

The measuring unit 150 may display the measured thickness of the NT of the fetus or the measured FMF angle on the display screen and thus, the operator or a physician may more accurately diagnose whether the fetus has an abnormality, based on the measured data.

When the sagittal view is redetermined by finely rotating the ultrasound data based on a manipulation of the operator, the measuring unit 150 may edit the measured thickness of the NT of the fetus, the measured FMF angle, a circumference of a figure matched with the image data, for example, a circumference of an oval, and the like.

Therefore, according to an embodiment, when the object is the fetus, the thickness of the NT of the fetus or the FMF angle between the dorsum nasi and the palate of the fetus are measured from the ultrasound data determined as the sagittal view and thus, whether the fetus has an abnormality may be accurately diagnosed.

In this example, the measuring unit 150 may focus on the NT of the fetus or the first feature point and the second feature point in the ultrasound data, using a predetermined color or a predetermined line and may display the focused data around the seed.

The method according to the above-described embodiments of the present invention may be recorded in non-transitory computer readable media including program instructions to implement various operations embodied by a computer. The media may also include, alone or in combination with the program instructions, data files, data structures, and the like. Examples of non-transitory computer readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter.

Although a few example embodiments have been shown and described, it would be appreciated by those skilled in the art that changes may be made in these example embodiments without departing from the principles and spirit of the invention, the scope of which is defined in the claims and their equivalents.

What is claimed is:

1. An ultrasound system, the system comprising:
  a scanner configured for scanning a human body to obtain ultrasound data including data for a plurality of reference images of A-plane, each of which illustrating a side of a fetus; and
  a controller configured to determine, as a mid-sagittal view image, a particular reference image from among the plurality of reference images by rotating the ultrasound data,
  wherein the particular reference image includes a falx region and a NT (nuchal translucency) region of the fetus.

2. The system of claim 1, wherein the controller is further configured to rotate the ultrasound data so that the particular reference image including the falx region with the highest brightness is to be identified.

3. The system of claim 1, wherein the controller is further configured to perform:
  determining, from the ultrasound data, a first feature point associated with a dorsum nasi of the fetus;
  determining, based on the first feature point, a second feature point associated with a palate of the fetus; and
  setting a center point of an object based on the determined second feature point.

4. The system of claim 1, wherein, when the object is the fetus, the system further comprises:
  a measuring unit configured to measure a thickness of the NT based on the determined mid-sagittal view.

5. The system of claim 1, wherein, when the object is the fetus, the system further comprises:
  a measuring unit configured to measure an angle between a first feature point associated with a dorsum nasi of the fetus and a second feature point associated with a palate of the fetus based on the determined mid-sagittal view image.

6. The system of claim 1, wherein the controller is further configured to finely rotate the ultrasound data based on a manipulation of an operator to redetermine the mid-sagittal view.

7. A method of operating a 3D ultrasound system, the method comprising:
  scanning a human body to obtain ultrasound data including data for a plurality of reference images of A-plane, each of which illustrating a side of a fetus; and
  determining via a controller, as a mid-sagittal view image, a particular reference image from among the plurality of reference images by rotating the ultrasound data,
  wherein the particular reference image includes a falx region and a NT (nuchal translucency) region of the fetus.

8. The method of claim 7, further comprising:
rotating the ultrasound data so that the particular reference image including the falx region with highest brightness is to be identified.

9. The method of claim 7, further comprising:
determining, from the ultrasound data, a first feature point associated with a dorsum nasi of the fetus;
determining, based on the first feature point, a second feature point associated with a palate of the fetus; and
setting a center point of an object based on the determined second feature point.

10. The method of claim 7, further comprising:
measuring a thickness of the NT based on the determined mid-sagittal view.

11. The method of claim 7, further comprising:
measuring an angle between a first feature point associated with a dorsum nasi of the fetus and a second feature point associated with a palate of the fetus based on the determined mid-sagittal view image.

12. The method of claim 7, further comprising:
redetermining the mid-sagittal view by finely rotating the ultrasound data based on a manipulation of an operator.

13. An ultrasound system, the system comprising:
a scanner configured for scanning an object inside a human body to obtain ultrasound data including data for a plane image displaying image data viewed from a head of a fetus;
a controller configured for determining a mid-sagittal view by rotating the ultrasound data so that an axis in a figure corresponding to the plane image is to be parallel with a predetermined axis.

14. The system of claim 13, wherein the figure is an oval, and
wherein the controller is further configured to rotate the ultrasound data to enable a major axis of the oval to be parallel with the predetermined axis.

15. The system of claim 14, wherein the controller is further configured to determine, as the mid-sagittal view, a side image displaying image data viewed from a right or left side of the fetus at a time when the axis in the figure corresponding to the plane image is to be parallel with the predetermined axis.

* * * * *